United States Patent
Kunz et al.

(10) Patent No.: US 11,475,989 B2
(45) Date of Patent: Oct. 18, 2022

(54) SYSTEMS AND METHODS TO PROCESS ELECTRONIC IMAGES TO PROVIDE AUTOMATED ROUTING OF DATA

(71) Applicant: PAIGE.AI, Inc., New York, NY (US)

(72) Inventors: Jeremy Daniel Kunz, New York, NY (US); Christopher Kanan, Rochester, NY (US); Patricia Raciti, New York, NY (US); Matthew G. Hanna, New York, NY (US)

(73) Assignee: PAIGE.AI, Inc., New York, NY (US)

(*) Notice: Subject to any disclaimer, the term of this patent is extended or adjusted under 35 U.S.C. 154(b) by 0 days.

(21) Appl. No.: 17/399,571

(22) Filed: Aug. 11, 2021

(65) Prior Publication Data

US 2022/0051783 A1    Feb. 17, 2022

Related U.S. Application Data

(60) Provisional application No. 63/064,714, filed on Aug. 12, 2020.

(51) Int. Cl.

| | |
|---|---|
| G06K 9/00 | (2022.01) |
| G16H 30/00 | (2018.01) |
| G16H 10/60 | (2018.01) |
| G16H 50/20 | (2018.01) |
| G06N 20/00 | (2019.01) |
| G16H 15/00 | (2018.01) |
| G06F 16/245 | (2019.01) |

(52) U.S. Cl.
CPC .......... *G16H 30/00* (2018.01); *G06F 16/245* (2019.01); *G06N 20/00* (2019.01); *G16H 10/60* (2018.01); *G16H 15/00* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 2007/0288260 A1 | 12/2007 | Burke et al. | |
| 2019/0189265 A1 | 6/2019 | Stoval et al. | |
| 2019/0267131 A1 | 8/2019 | Dehghan et al. | |
| 2020/0126207 A1* | 4/2020 | Saltz | G06V 20/695 |
| 2020/0160510 A1* | 5/2020 | Lindemer | G06K 9/629 |
| 2020/0160941 A1 | 5/2020 | Sharma et al. | |
| 2021/0090694 A1* | 3/2021 | Colley | G16B 40/00 |

OTHER PUBLICATIONS

Jianxing He, Sally L. Baxter, Jie Xu, Jiming Xu, Xingtao Zhou & Kang Zhang; The practical implementation of artificial intelligence technologies in medicine; Nature Medicine | vol. 251 Jan. 2019 130-36 (Year: 2019).

Wikipedia, IBM Watson Health, Apr. 16, 2020 (Year: 2020).

* cited by examiner

*Primary Examiner* — Wei Wen Yang
(74) *Attorney, Agent, or Firm* — Bookoff McAndrews, PLLC.

(57) ABSTRACT

Systems and methods are disclosed for providing automated routing of medical data, comprising determining at least one rule corresponding to at least one condition and at least one receiver, receiving medical data and associated medical metadata, determining whether the medical data, the associated medical metadata, and/or associated artificial intelligence processing satisfies the at least one condition of the at least one rule, and upon determining that the at least one condition of the at least one rule is satisfied, providing, from an originating institution, the medical data to the at least one receiver.

20 Claims, 7 Drawing Sheets

SYSTEMS AND METHODS TO PROCESS ELECTRONIC IMAGES TO PROVIDE AUTOMATED ROUTING OF DATA

RELATED APPLICATION(S)

This application claims priority to U.S. Provisional Application No. 63/064,714 filed Aug. 12, 2020, the entire disclosure of which is hereby incorporated by reference in its entirety.

FIELD OF THE DISCLOSURE

Various embodiments of the present disclosure pertain generally to image processing methods. More specifically, particular embodiments of the present disclosure relate to systems and methods for automatically routing data based on processing images of tissue specimens.

BACKGROUND

Routing medical data to a correct set of recipients is important for fast and accurate diagnosis. With non-digital medical data, it may be challenging to send a sample to a qualified expert. For example, in histopathology, glass slides may have to be physically moved so that an expert may review them. If the preferred expert is outside of the originating hospital or clinic, there may be significant delay before an expert may receive the glass slides, or a non-preferred expert may be selected because they are physically closer to the originating institution. However, as more forms of medical data become digital, they may be more efficiently routed to an optimal expert or set of experts for diagnosis and analysis. For example, in pathology, a whole slide image (WSI), a high-fidelity version of a glass slide, may be digitally routed to an expert sub-specialist pathologist for feedback and/or a second opinion on the case. The same may be true for neurology (e.g., an electroencephalography recording) and radiology (e.g., an MRI or CT scan), where sub-specialist experts may be called upon to make a definitive analysis of the digital medical data. Techniques presented herein may be important for rare conditions (e.g., rare kinds of tumors) and other similar scenarios.

If medical data is routed to a professional who lacks sufficient expertise, this may lead to inefficiencies in the workflow of the diagnostic center, may result in a slower diagnosis for the patient at greater expense, or may increase the likelihood of a misdiagnosis.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for a routing system for medical data.

A computer-implemented method for providing automated routing of medical data comprises determining at least one rule corresponding to at least one condition and at least one receiver, receiving medical data and associated medical metadata, determining whether the medical data, the associated medical metadata, and/or associated artificial intelligence processing satisfies the at least one condition of the at least one rule, and upon determining that the at least one condition of the at least one rule is satisfied, providing, from an originating institution, the medical data to the at least one receiver.

A computer system for providing automated routing of medical data comprises at least one memory storing instructions, and at least one processor configured to execute the instructions to perform operations comprising: determining at least one rule corresponding to at least one condition and at least one receiver, receiving medical data and associated medical metadata, determining whether the medical data, the associated medical metadata, and/or associated artificial intelligence processing satisfies the at least one condition of the at least one rule, and upon determining that the at least one condition of the at least one rule is satisfied, providing, from an originating institution, the medical data to the at least one receiver.

A non-transitory computer-readable medium storing instructions that, when executed by a processor, cause the processor to perform operations for routing medical data, the operations comprising: determining at least one rule corresponding to at least one condition and at least one receiver, receiving medical data and associated medical metadata, determining whether the medical data, the associated medical metadata, and/or associated artificial intelligence processing satisfies the at least one condition of the at least one rule, and upon determining that the at least one condition of the at least one rule is satisfied, providing, from an originating institution, the medical data to the at least one receiver.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1A:
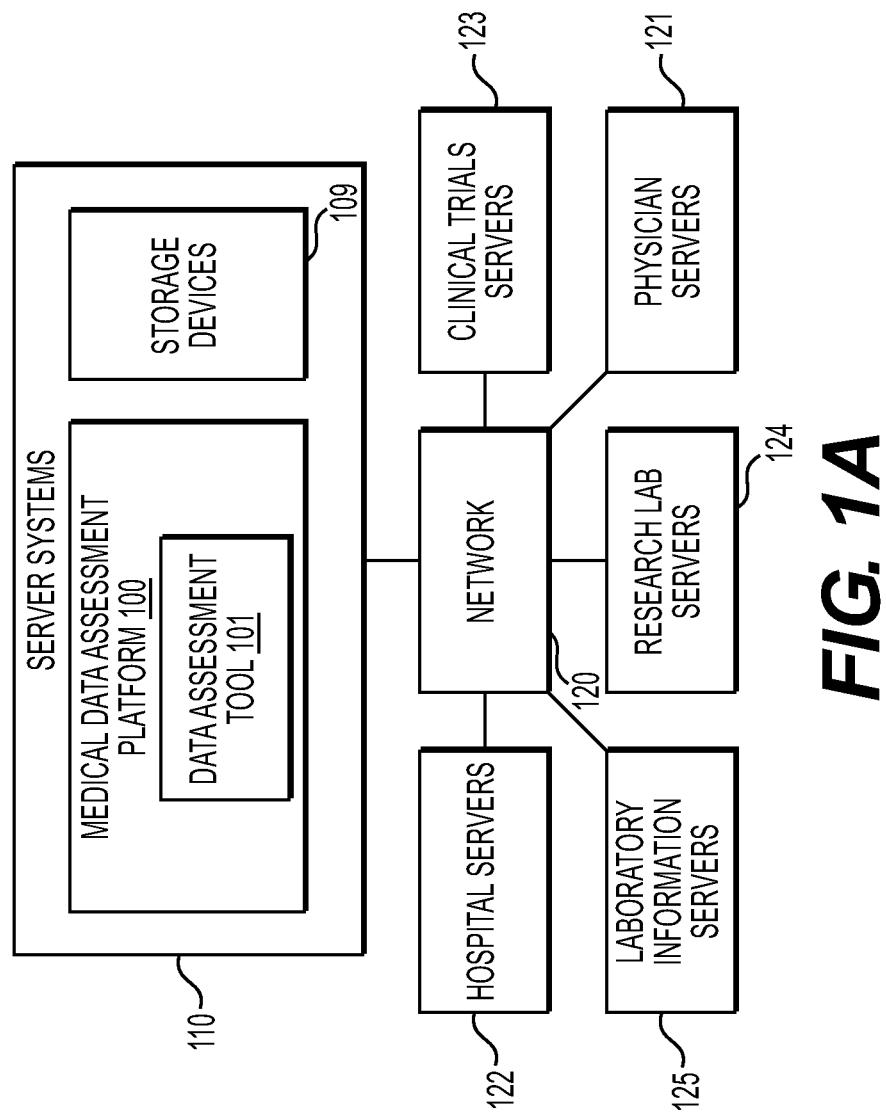
FIG. 1A illustrates an exemplary block diagram of a system and network for medial data routing, according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Artificial intelligence (AI) systems are becoming more widely used to assess medical data, but they may not be able to correctly process rarer conditions. If the AI system is uncertain it may triage the case to send it to a qualified expert for diagnosis. One or more embodiments of the present disclosure may solve the above problems. For example, one or more embodiments may provide methods for systematic routing of medical data to appropriate experts. Many areas of medicine may be improved by speeding up the time for diagnosis in areas where there is a lack of expertise in a center.

The present disclosure relates to routing medical data to an expert for assessment based on a set of criteria, a manual intervention, or an AI-based assessment of the medical data. For example, the present disclosure relates to using AI or a set of established rules to route medical data to an appropriate entity for a review that may include diagnosis, treatment recommendation, or analysis. Medical data may be medical records (e.g., text), medical images (e.g., digital microscopy, whole slide images, x-ray scans, MRI scans, CT scans, etc.), genetic testing, genomic testing, etc.

Exemplary embodiments may use a rule-based configuration file that communicates with a scanner/laboratory information system (LIS). Exemplary embodiments may be used in hospitals, veterinarians, clinics, labs. Based on the configuration file, the medical data may be transferred using a digital storage device (e.g., hard drive, network drive, cloud storage, RAM, etc.).

Patient care may be improved by improving the quality of the assessment of digital medical data by a qualified expert, resulting in an improved diagnosis/treatment and a reduction of errors. Additionally, turnaround time may be reduced because the expert may be determined automatically, so patients may get a diagnosis faster. Exemplary embodiments may be integrated with a platform used for viewing digital microscopy cases in either research or clinical (e.g., hospital or veterinarian) settings.

One or more embodiments relate to a routing system for medical data. The input to the system may be medical data and associated information. Exemplary embodiments may be used for arbitrary forms of medical data, which may include, but are not limited to, digitized pathology images such as a whole slide images (WSI), static images, patient medical records, physician notes, radiological scans, dental notes, and/or lab results, etc. In addition, a set of recipients may be defined. Recipients may be a specific person in the originating center, a department in the center, or an external entity (e.g., an individual or group of individuals at a different hospital or clinic).

FIG. 1A illustrates an exemplary block diagram of a system and network for routing medical data, using machine learning, according to an exemplary embodiment of the present disclosure.

Specifically, FIG. 1A illustrates an electronic network 120 that may be connected to servers at hospitals, veterinarians, laboratories and/or doctor's offices, etc. For example, physician servers 121, hospital servers 122, clinical trial servers 123, research lab servers 124, and/or laboratory information systems 125, etc., may each be connected an electronic network 120, such as the Internet, through one or more computers, servers and/or handheld mobile devices. According to an exemplary embodiment of the present application, the electronic network 120 may also be connected to server systems 110, that may include processing devices that are configured to implement a medical data assessment platform 100, which includes a data assessment tool 101 for determining specimen property or image property information pertaining to medical data, and using machine learning to determine routing information for the medical data, according to an exemplary embodiment of the present disclosure.

The physician servers 121, hospital servers 122, clinical trial servers 123, research lab servers 124 and/or laboratory information systems 125 refer to systems used by pathologists for reviewing the images of the slides. In hospital settings, tissue type information may be stored in a laboratory information system 125.

Figure 1B:
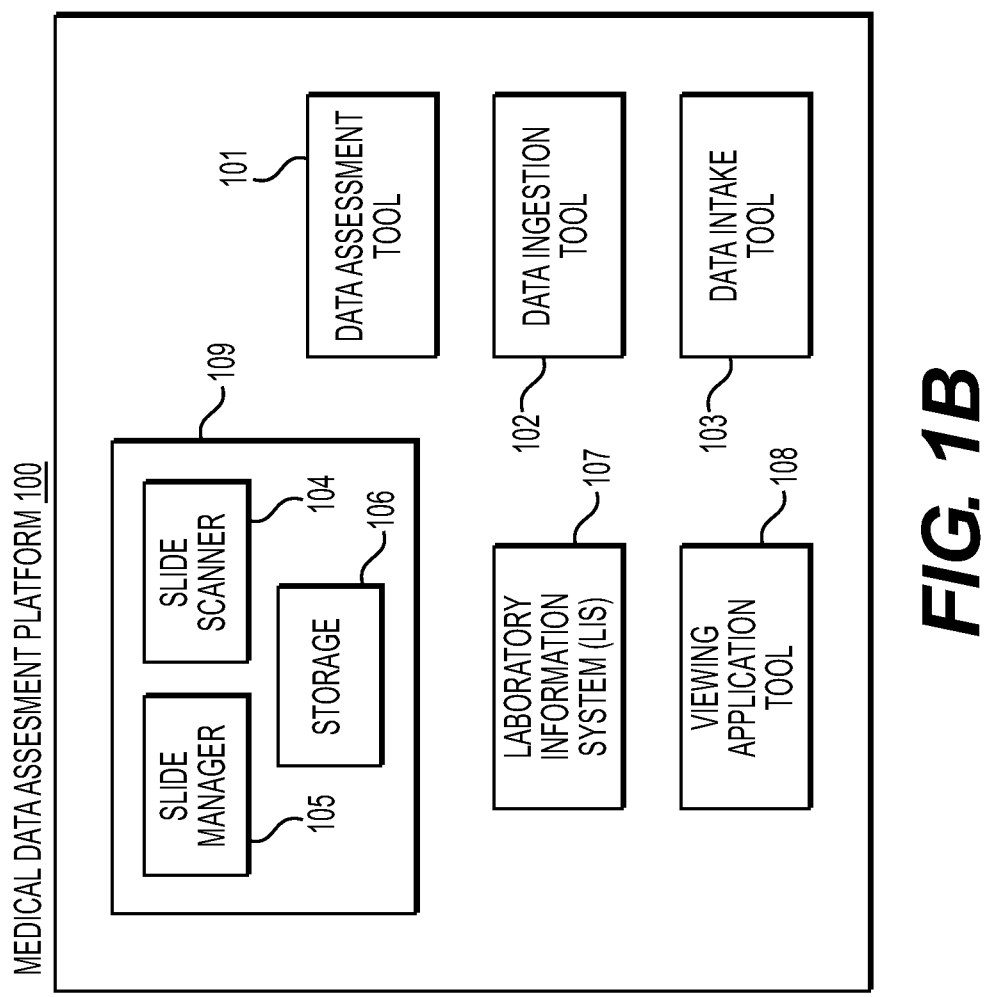
FIG. 1B illustrates an exemplary block diagram of a medical data assessment platform, according to an exemplary embodiment of the present disclosure.

FIG. 1B illustrates an exemplary block diagram of a medical data assessment platform 100 for routing medical data, using machine learning. The medical data assessment platform 100 may include a data assessment tool 101, a data ingestion tool 102, a slide intake tool 103, a slide scanner 104, a slide manager 105, a storage 106, a laboratory information system 107 and a viewing application tool 108.

The data assessment tool 101, as described below, refers to a process and system for determining data variable property or health variable property information pertaining to digital pathology image(s). Machine learning may be used to classify an image, according to an exemplary embodiment.

The data ingestion tool 102 may facilitate a transfer of the digital pathology images to the various tools, modules, components, and devices that are used for classifying and processing the digital pathology images, according to an exemplary embodiment.

The slide intake tool 103 may scan pathology images and convert them into a digital form, according to an exemplary embodiment. The slides may be scanned with slide scanner 104, and the slide manager 105 may process the images on the slides into digitized pathology images and store the digitized images in storage 106.

The viewing application tool 108 may provide a user with a specimen property or image property information pertaining to digital pathology image(s), according to an exemplary embodiment. The information may be provided through various output interfaces (e.g., a screen, a monitor, a storage devices and/or a web browser, etc.).

The data assessment tool 101, and one or more or its components, may transmit and/or receive digitized slide images and/or patient information to server systems 110, physician servers 121, hospital servers 122, clinical trial servers 123, research lab servers 124, and/or laboratory information systems 125 over an electronic network 120. Further, server systems 110 may include storage devices 109 for storing images and data received from at least one of the data assessment tool 101, the data ingestion tool 102, the slide intake tool 103, the slide scanner 104, the slide manager 105, and viewing application tool 108. Server systems 110 may also include processing devices for processing images and data stored in the storage devices 109. Server systems 110 may further include one or more machine learning tool(s) or capabilities, e.g., due to the processing devices. Alternatively, or in addition, the present disclosure (or portions of the systems and methods of the present disclosure) may be performed on a local processing device (e.g., a laptop).

Any of the above devices, tools and modules may be located on a device that may be connected to an electronic network such as the Internet or a cloud service provider, through one or more computers, servers and/or handheld mobile devices.

Figure 1C:
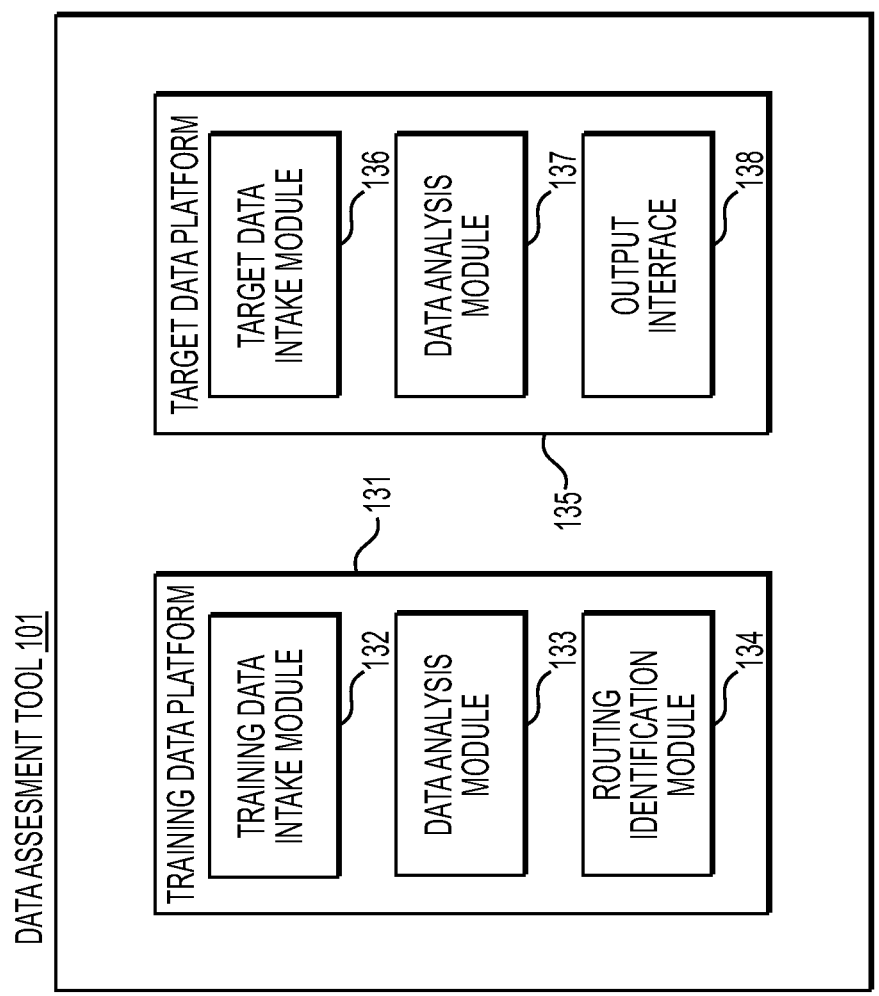
FIG. 1C illustrates an exemplary block diagram of a data assessment tool, according to an exemplary embodiment of the present disclosure.

FIG. 1C illustrates an exemplary block diagram of a data assessment tool 101, according to an exemplary embodiment of the present disclosure. The data assessment tool 101 may include a training data platform 131 and/or a target data platform 135.

According to one embodiment, the training data platform 131 may include a training data intake module 132, a data analysis module 133, and a routing identification module 134.

The training data platform 131, according to one embodiment, may create or receive training data that are used to train a machine learning model to effectively analyze and classify digital pathology images in accordance with user-defined rules. For example, training data may be received from any one or any combination of the server systems 110, physician servers 121, hospital servers 122, clinical trial servers 123, research lab servers 124, and/or laboratory information systems 125. Data used for training may come from real sources (e.g., humans, animals, etc.) or may come from synthetic sources (e.g., graphics rendering engines, 3D models, etc.). Examples of data may include (a) digitized slides stained with a variety of stains, such as (but not limited to) H&E, Hematoxylin alone, IHC, molecular pathology, etc.; and/or (b) digitized tissue samples from a 3D imaging device, such as microCT.

The training data intake module 132 may create or receive a dataset comprising one or training datasets corresponding to digital pathology slides or other forms of medical data. For example, the training datasets may be received from any one or any combination of the server systems 110, physician servers 121, hospital servers 122, clinical trial servers 123, research lab servers 124, and/or laboratory information systems 125. This dataset may be kept on a digital storage device. The data analysis module 133 may identify quality control (QC) issues (e.g., imperfections) for the training datasets at a global or local level that may affect the usability of a dataset. For example, the quality score determiner module may use information about an entire dataset, e.g., the dataset type, the overall quality of the cut of the specimen, the overall quality of the dataset itself, or pathology slide characteristics, and determine an overall quality score for the dataset. The routing identification module 134 may analyze medical data to determine whether the medical data meets the rule set by the user. Determining whether medical data meets a rule, and in turn should be routed to a recipient, is important for fast and accurate diagnoses.

According to one embodiment, the target data platform 135 may include a target data intake module 136, a routing analysis module 137, and an output interface 138. The target data platform 135 may receive a target dataset and apply the machine learning model to the received target data to determine a characteristic of a target data set. For example, the target data may be received from one or any combination of the server systems 110, physician servers 121, hospital servers 122, clinical trial servers 123, research lab servers 124, and/or laboratory information systems 125. The target data intake module 136 may receive a target dataset corresponding to a target medical dataset. The routing analysis module 137 may apply the machine learning model to the target dataset to determine a characteristic of the target medical dataset. For example. The routing analysis module 137 may also apply the machine learning model to the target dataset to determine a quality score for the target dataset.

The output interface 138 may be used to output information about the target data and the routing rule (e.g., to a screen, monitor, storage device, web browser, etc.).

Figure 2:
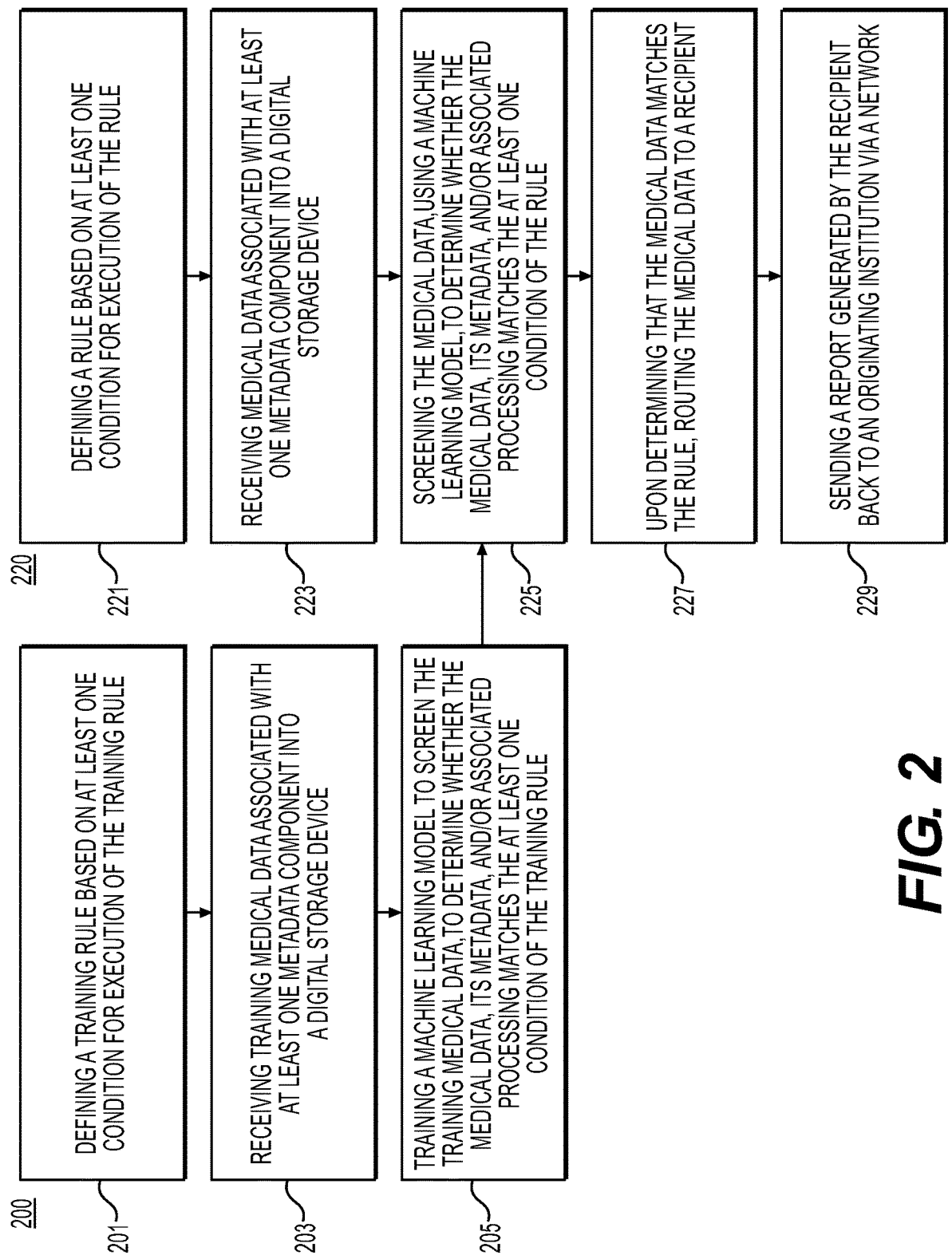
FIG. 2 illustrates an exemplary method of training and using a routing system for medical data, according to an exemplary embodiment of the present disclosure.

FIG. 2 illustrates an exemplary method of training and using a routing system for medical data, using machine learning. According to one or more exemplary embodiments, a set of rules may be defined such that, if a piece of medical data satisfies a specific criterion, it may be routed to a pre-defined entity for reviewing that piece of medical data. The rule may be automatically executed, or it may be manually invoked by a user. For example, exemplary method 200 (e.g., steps 201-205) and exemplary method 220 (e.g., steps 221-229) may be performed by data assessment tool 101 automatically or in response to a request from a user.

According to one embodiment, the exemplary method 200 for training a machine learning model for routing medical data may include one or more of the following steps. In step 201, the method may include defining a training rule based on at least one condition for execution of the training rule. A set of rules may be defined such that, if a piece of medical data satisfies a specific criterion, it may be routed to a pre-defined entity for reviewing the piece of medical data. The rule may be automatically executed, or it may be manually invoked by a user. Users (e.g., individual physicians, the hospital, technicians, administrator, etc.) in an originating institution may specify a set of conditions for executing the rule. The conditions may be in the form of the disease, the tissue type, the location of the sample, the physician assigned to review it at the originating institution, the output of an AI-based system not being able to make the diagnosis on the medical data with an adequate level of confidence, etc. For each rule, a set of receivers may be defined. Receivers may be internal or external to the originating institution. Receivers may be an individual or a group of individuals such as an entire medical department or a company. Receivers may be defined to have a specific skillset or expertise to receive the medical data for assessment.

In step 203, the method may include receiving training medical data associated with at least one metadata component (e.g., the tissue type, disease type, tissue location, etc.) into a digital storage device (e.g., hard drive, network drive, cloud storage, RAM, etc.).

In step 205, the method may include training a machine learning model to screen the training medical data to determine whether the training medical data, its metadata, and/or associated processing matches the at least one condition of the training rule.

The exemplary method 220 of using the routing system may include one or more of the following steps. In step 221, the method may include defining a rule based on at least one condition for execution of the rule. A set of rules may be defined such that, if a piece of medical data satisfies a specific criterion, it may be routed to a pre-defined entity for reviewing the piece of medical data. The rule may be automatically executed, or it may be manually invoked by a user. Users (e.g., individual physicians, the hospital, technicians, administrator, etc.) in an originating institution may specify a set of conditions for executing the rule. The conditions may be in the form of the disease, the tissue type, the location of the sample, the physician assigned to review it at the originating institution, the output of an AI-based system not being able to make the diagnosis on the medical data with an adequate level of confidence, etc. For each rule, a set of receivers may be defined. Receivers may be internal or external to the originating institution. Receivers may be an individual or a group of individuals such as an entire medical department or a company. Receivers may be defined to have a specific skillset or expertise to receive the medical data for assessment.

In step 223, the method may include receiving medical data associated with at least one associated metadata component (e.g., the tissue type, disease type, tissue location, etc.) into a digital storage device (e.g., hard drive, network drive, cloud storage, RAM, etc.).

In step 225, the method may include screening the medical data, using a machine learning model, to determine whether the medical data, its metadata, and/or associated processing matches the at least one condition of the rule.

In step 227, the method may include, upon determining that the medical data matches the rule, routing the medical data to a recipient. If the medical data, its metadata, and/or associated processing (e.g., by an AI based system) matches the criteria, then the medical data may be routed to the recipient or set of recipients specified in the rule, e.g., via the cloud, an internet connection, and/or a local area network, etc. Invocation of the routing rule if the conditions are met may occur automatically or may be done by the user, e.g., by clicking a button to cause the routing to occur.

In step 229, the method may include sending a report generated by the recipient back to an originating institution via a network. The recipient may review the medical data after receipt of the medical data from the originating institution, which may include automatically adding a case to a list of cases to review by an expert panel/consensus conference, and scheduling any possibly required calendar events with any possible necessary video communications with plugins. After the recipient reviews the medical data, their report may be sent back to the originating institution via the cloud, an internet connection, and/or a local area network, etc.

Exemplary Embodiment: WSI of Histopathology Specimens: In many situations, the pathologist who staffs a care center may not have adequate expertise to render the correct diagnosis. For example, this situation may happen when a sub-specialist would be strongly preferred, e.g., skin pathology, or for tissue types where cancer is uncommon or difficult to diagnose, e.g., melanoma, where there may be only a small number of pathologists in the world who are experts in a tissue type. According to an exemplary embodiment, the input may be a set of digital whole slide images (WSIs) of a pathology specimen from a patient, which may then be routed to a qualified expert.

1. Rules for routing a WSI may be defined as:
   a. Users specify categorical fields for executing the rule on the WSI. They may list the conditions that the WSI needs to satisfy for the rule to be executed, which may be the form of disease, the tissue type, the location of the sample, the pathologist assigned to review it at the originating institution, the output of an AI-based system not being able to make the diagnosis on the WSIs with an adequate level of confidence, etc.
   b. For each rule, a set of receivers may be defined. Receivers may be internal or external to the originating institution. Receivers may be an individual pathologist or a group of pathologists such as an entire medical department or company. Receivers may be defined to have a specific skillset or expertise to receive the medical data for assessment.
2. Receive pathology data into a digital storage device (e.g., hard drive, network drive, cloud storage, RAM, etc.) with associated metadata, e.g., the tissue type, disease type, tissue location, etc.
3. If the pathology data, its metadata, and/or associated processing (e.g., by an AI based system) matches the criteria, then the medical data may be routed to the recipient or set of recipients specified in the rule, e.g., via the cloud, an internet connection, and/or a local area network, etc. Invocation of the rule may occur automatically or may be done by the user, e.g., by clicking a button to cause the routing to occur (see FIG. 1).
4. The recipient receives the data for review, which may include automatically adding a case to a list of cases to review by an expert panel/consensus conference, scheduling any possibly required calendar events with any possibly necessary video communications with plugins, etc.
5. After the recipient(s) reviews the medical data, their report may be sent back to the originating institution via the cloud, an internet connection, and/or a local area network, etc.

Figure 3:
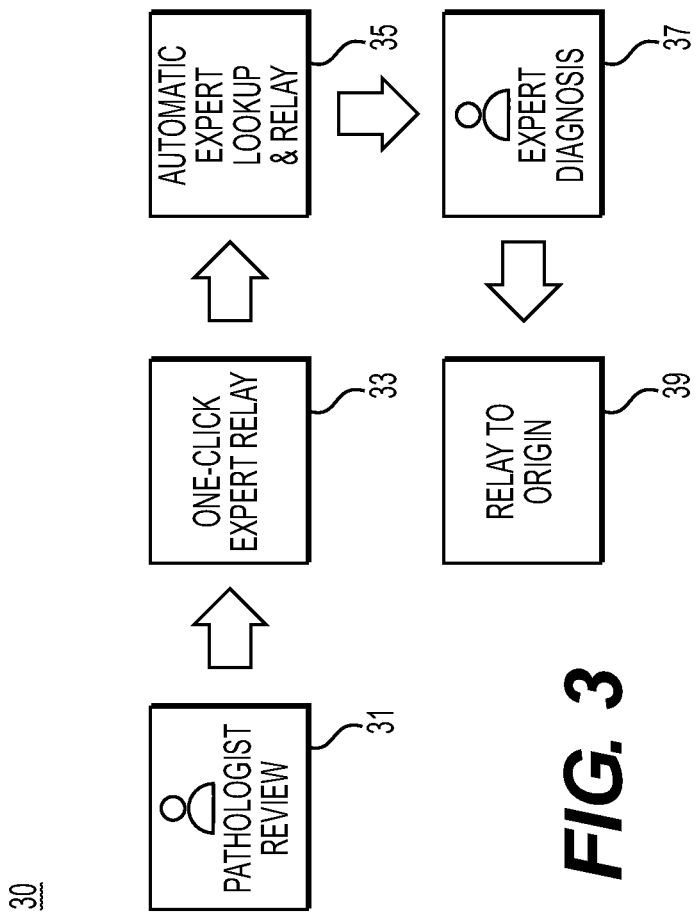
FIG. 3 illustrates an overview of an execution workflow of an exemplary embodiment, according to an exemplary embodiment of the present disclosure.

FIG. 3 illustrates an overview of an execution workflow of an exemplary embodiment, according to an exemplary embodiment of the present disclosure.

According to an exemplary embodiment illustrated in FIG. 3, the workflow 30 (e.g., steps 31-39) may include a pathologist invoking pre-specified rules, e.g., by clicking a button, for a set of digital pathology data to be assessed by an expert or set of experts. The experts review the data and then relay it back to the original pathologist.

In step 31, the pathologist at the originating institution may review the medical data for an instant patient or case. The pathologist may determine that an expert review is necessary, or a rule may determine that expert review is necessary.

In step 33, one-click expert relay may be initiated. If the pathologist or rule determines that expert review is needed, the pathologist may use the one-click expert relay to send the medical data to an expert at a different location or different workspace.

In step 35, the workflow may include an automatic expert lookup and relay, where the pathologist user of the system does not need to manually find an appropriate expert and send the medical data to another location.

In step 37, the workflow may include expert review and rendering of a diagnosis based on the provided medical data.

In step 39, the workflow may include relaying an expert's back to the originating physician.

Figure 4:
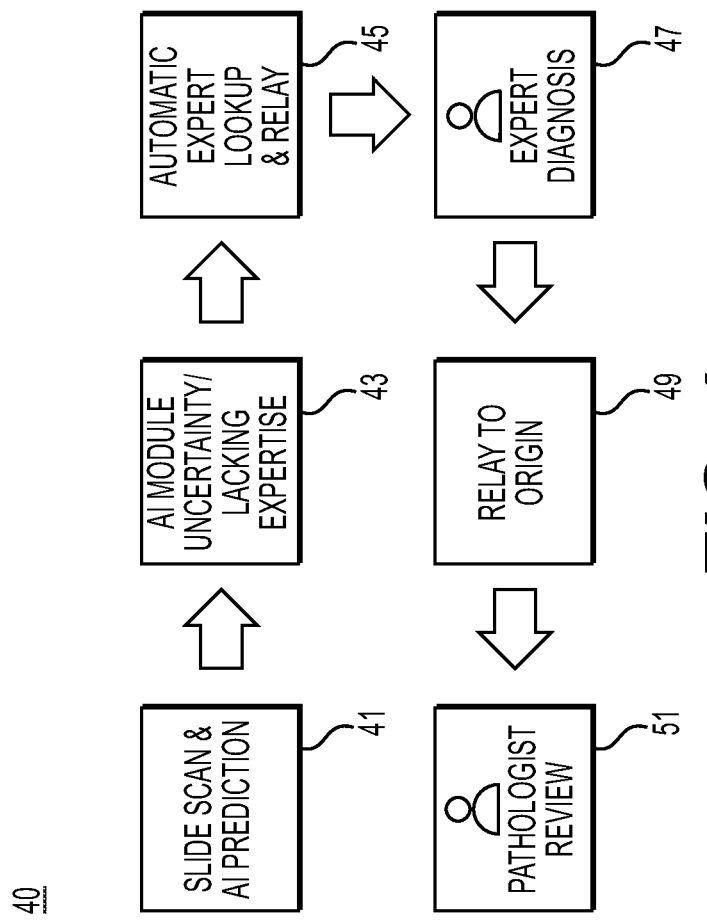
FIG. 4 illustrates an overview of an execution workflow of an exemplary embodiment, according to an exemplary embodiment of the present disclosure.

FIG. 4 illustrates an overview of an execution workflow 40 of an exemplary embodiment of the present disclosure.

According to an exemplary embodiment illustrated in FIG. 4, an AI-based system screens the pathology data automatically. If it is determined that the AI-based system cannot accurately diagnose the data (e.g., because it is a rare form of cancer), then it may route the data to an expert or set of experts for review, who may then relay their opinion back to the original institution.

In step 41, the workflow may include scanning slides may be scanned into a system by the slide scanner 104 to yield an AI prediction from the system.

In step 43, the workflow may include determining that the AI prediction is uncertain or lacking expertise in an identified disease, such as in the case of rare cancers. A rule may be applied so that if a rare cancer is detected, the system will recognize that the AI prediction has a high degree of uncertainty.

In step 45, the workflow may include, upon determining that the AI module lacks certainty or expertise, the system automatically looking up an expert and relaying the slide images to that expert.

In step 47, the workflow may include expert review of the relayed slide images and determining a diagnosis for the images.

In step 49, the workflow may include relaying the expert diagnosis back to the originating location and physician.

In step 51, the workflow may include the originating physician reviewing the expert diagnosis and determining a treatment track.

Exemplary Embodiment: Radiology: In many situations the radiologist who staffs a care center may not have adequate expertise to do the diagnosis. For example, this situation may happen when a sub-specialist would be essential, e.g., breast cancer. This may be important for rare diseases and conditions where there are only a small number of radiologists in the world are experts. The input to the system would be radiology scans from a patient and associated patient data. In radiology, rule based routing may be performed depending on the methodology such as Mammography, Sonography, positron emission tomography (PET), magnetic resonance imaging (MRI), computer tomography (CT), fluoroscopy, bone density scanning, and/or dual-energy x-ray absorptiometry (DXA). Routing may also be performed based on the hardware manufacturer. Furthermore, a digital radiology image may be routed based on the radiologist's specialty such as abdominal, breast, cardiac, musculoskeletal, thoracic and/or neuroradiology. Emergency radiology samples may be automatically routed to unoccupied radiologists or expert radiologists for an additional review. In dental radiology, at a dentist, the dental x-ray may be routed to the correct subspecialty based on the dentist, patient history and/or certified dental assistant. The exact routing rules may be defined depending on the requirements of the dentist office. In this embodiment, the input may be a set of digital radiological data (e.g., MRI scans, CT scans, X-ray scans, PET scans, etc.) from a patient, which may then be routed to a qualified expert.

The steps for an exemplary embodiment for radiology may be as follows:
1. Rules for routing may be defined as:
    a. Users specify categorical fields for executing the rule on the radiology data. They list the conditions that the radiological data may need to satisfy for the rule to be executed, which may be the form of disease, the tissue type, the location of the sample, the pathologist assigned to review it at the originating institution, and/or the output of an AI-based system not being able to make the diagnosis on the data with an adequate level of confidence, etc. An AI system may also be used to identify that there may be inadequate expertise in a center for a given radiological scan, then it may do the routing automatically. For example, if a dental center lacks the expertise for a condition, such as bone loss, unusual wisdom teeth, cavities, infections, and/or cysts or tumors, then the scans (e.g., x-rays from the patient) may be automatically detected by the AI system and routed to an expert within or outside of the medical center.
    b. For each rule, a set of receivers may be defined. Receivers may be internal or external to the originating institution. Receivers may be an individual radiologist or a group of radiologists such as an entire medical department or company. Receivers may be defined to have a specific skillset or expertise to receive the medical data for assessment.
2. Receive radiology data into a digital storage device (e.g., hard drive, network drive, cloud storage, RAM, etc.) with associated metadata, e.g., the tissue type, disease type, tissue location, etc.
3. If the radiology data, its metadata, and/or associated processing (e.g., by an AI based system) matches the criteria, then the radiology data may be routed to the recipient or set of recipients specified in the rule, e.g., via the cloud, an internet connection, and/or a local area network, etc. Invocation of the rule may occur automatically or may be done by the user, e.g., by clicking a button to cause the routing to occur.
4. The recipient receives the data for review, which may include automatically adding a case to a list of cases to review by an expert panel/consensus conference, scheduling any possibly required calendar events with any possibly necessary video communications with plugins, etc.
5. After the recipient(s) reviews the medical data, their report may be sent back to the originating institution via the cloud, an internet connection, and/or a local area network, etc.

Exemplary Embodiment: Medical Records and History Routing: In all areas of medicine, notes and records may be taken in digitized text by a physician. In this embodiment, these records may be routed to a qualified expert for review. The input to the system may be the text-based medical data taken from the patient and associated data. The input to this embodiment may be medical metadata including some or all related documents, diagnosis, and lab result documents.

The steps for this embodiment may be as follows:
1. Rules for routing may be defined as:
    a. Users (e.g., individual physicians, the hospital, technician, administrator, etc.) specify categorical fields for executing the rule on the medical record data. Rules may be based on specific keywords, professionals (trainee), tissue types, disease conditions, submitting clinician, case ID, accession number, etc. Alternatively, an AI system may detect unusual lab measurements or other reporting information causing the medical data to automatically be routed to an expert.
    b. For each rule, a set of receivers may be defined. Receivers may be internal or external to the originating institution. Receivers may be an individual clinician or a group of clinicians such as an entire medical department or company. Receivers may be defined to have a specific skillset or expertise to receive the medical data for assessment.

2. Receive medical data into a digital storage device (e.g., hard drive, network drive, cloud storage, RAM, etc.).
3. If the medical data, its metadata, and/or associated processing (e.g., by an AI based system) matches the criteria, then the data may be routed to the recipient or set of recipients specified in the rule, e.g., via the cloud, an internet connection, and/or a local area network, etc. Invocation of the rule may occur automatically or may be done by the user, e.g., by clicking a button to cause the routing to occur.
4. The recipient receives the data for review, which may include automatically adding a case to a list of cases to review by an expert panel/consensus conference, scheduling any possibly required calendar events with any possibly necessary video communications with plugins, etc.
5. After the recipient(s) reviews the medical data, their report may be sent back to the originating institution via the cloud, an internet connection, and/or a local area network, etc.

Exemplary Embodiment: Omics data: Genomic sequencing of tumors and genetic testing of patients, including fetuses, is commonly done to help identify mutations of concern. However, for rarer mutations a center may not have adequate expertise to understand the results of these assays. This embodiment routes this data to an expert with the requisite expertise for interpreting the outcome of the genetic or genomic assay. Using this embodiment, the digital case (including all related genetic information) may be routed to the correct subspecialty or clinical geneticist based on accession number, case ID, mutations, microsatellite instabilities, copy number variations, gene expressions, methylation status, method (whole genome sequencing, RNA-seq, 16s microbiome sequencing, bisulfite sequencing), part type and/or submitted clinician. In medical genetics and genomics, at a hospital, the digital case (including all related genetic information) may be routed to the correct subspecialty or clinical geneticist based on the genetic or genomic data. The exact routing rules may be defined depending on the requirements of the hospital. An individual clinical geneticist may also setup a set of rules to route cases and get notified once specific conditions occur such as rare mutations, presence of specific coding and non-coding genes or intergenic and intronic single-nucleotide polymorphisms.

The steps for this embodiment may be as follows:
1. Rules for routing may be defined as:
   a. Users (e.g., individual physicians/geneticists, the hospital, veterinarian, technician, administrator, etc.) specify categorical fields for executing the rule on the medical data. Rules may be based on specific tissue types, mutations, microsatellite instabilities, copy number variations, gene expressions, methylation status, disease conditions, etc. Alternatively, an AI system may detect unusual genetic or genomic patterns causing the medical data to automatically be routed to an expert.
   b. For each rule, a set of receivers may be defined. Receivers may be internal or external to the originating institution. Receivers may be an individual or a group of individuals (physicians or geneticists) such as an entire medical department or company. Receivers may be defined to have a specific skillset or expertise to receive the medical data for assessment.
2. Receive medical data into a digital storage device (e.g., hard drive, network drive, cloud storage, RAM, etc.).
3. If the medical data, its metadata, and/or associated processing (e.g., by an AI based system) matches the criteria, then the data may be routed to the recipient or set of recipients specified in the rule, e.g., via the cloud, an internet connection, and/or a local area network, etc. Invocation of the rule may occur automatically or may be done by the user, e.g., by clicking a button to cause the routing to occur.
4. The recipient receives the data for review, which may include automatically adding a case to a list of cases to review by an expert panel/consensus conference, scheduling any possibly required calendar events with any possibly necessary video communications with plugins, etc.
5. After the recipient(s) reviews the medical data, their report may be sent back to the originating institution via the cloud, an internet connection, and/or a local area network, etc.

Exemplary Embodiment: Digital Microscopy: To diagnose many diseases slides of samples taken from patients may be used to make the diagnosis or to guide treatment. For example, histology slides, cytology slides, fluorescence in situ and/or hybridization slides, etc., may be used. Using digital microscopy, these specimens may be turned into digital images that may then be reviewed by an expert or an AI system. In this embodiment, the system takes as input digital microscopy image(s) and then routes the image(s) and associated patient data to the appropriate entity for additional analysis, diagnosis, and/or treatment recommendation. The input to this embodiment may be the set of digital microscopy images and associated medical data.

The steps for this embodiment may be as follows:
1. Rules for routing may be defined as:
   a. Users specify categorical fields for executing the rule on the digital microscopy data. Alternatively, if an AI module has a high level of uncertainty or detects a challenging condition (e.g. unique Pap smear, uncertain viability of cells such as embryo cells) for a digital microscopy mage, the slide may be set to automatically be routed to an expert.
   b. For each rule, a set of receivers may be defined. Receivers may be internal or external to the originating institution. Receivers may be an individual or a group of individuals such as an entire medical department or company. Receivers may be defined to have a specific skillset or expertise to receive the medical data for assessment.
2. Receive medical data into a digital storage device (e.g., hard drive, network drive, cloud storage, RAM, etc.).
3. If the medical data, its metadata, and/or associated processing (e.g., by an AI based system) matches the criteria, then the data may be routed to the recipient or set of recipients specified in the rule, e.g., via the cloud, an internet connection, and/or a local area network, etc. Invocation of the rule may occur automatically or may be done by the user, e.g., by clicking a button to cause the routing to occur.
4. The recipient receives the data for review, which may include automatically adding a case to a list of cases to review by an expert panel/consensus conference, scheduling any possibly required calendar events with any possibly necessary video communications with plugins, etc.
5. After the recipient(s) reviews the medical data, their report may be sent back to the originating institution via the cloud, an internet connection, and/or a local area network, etc.

Figure 5:
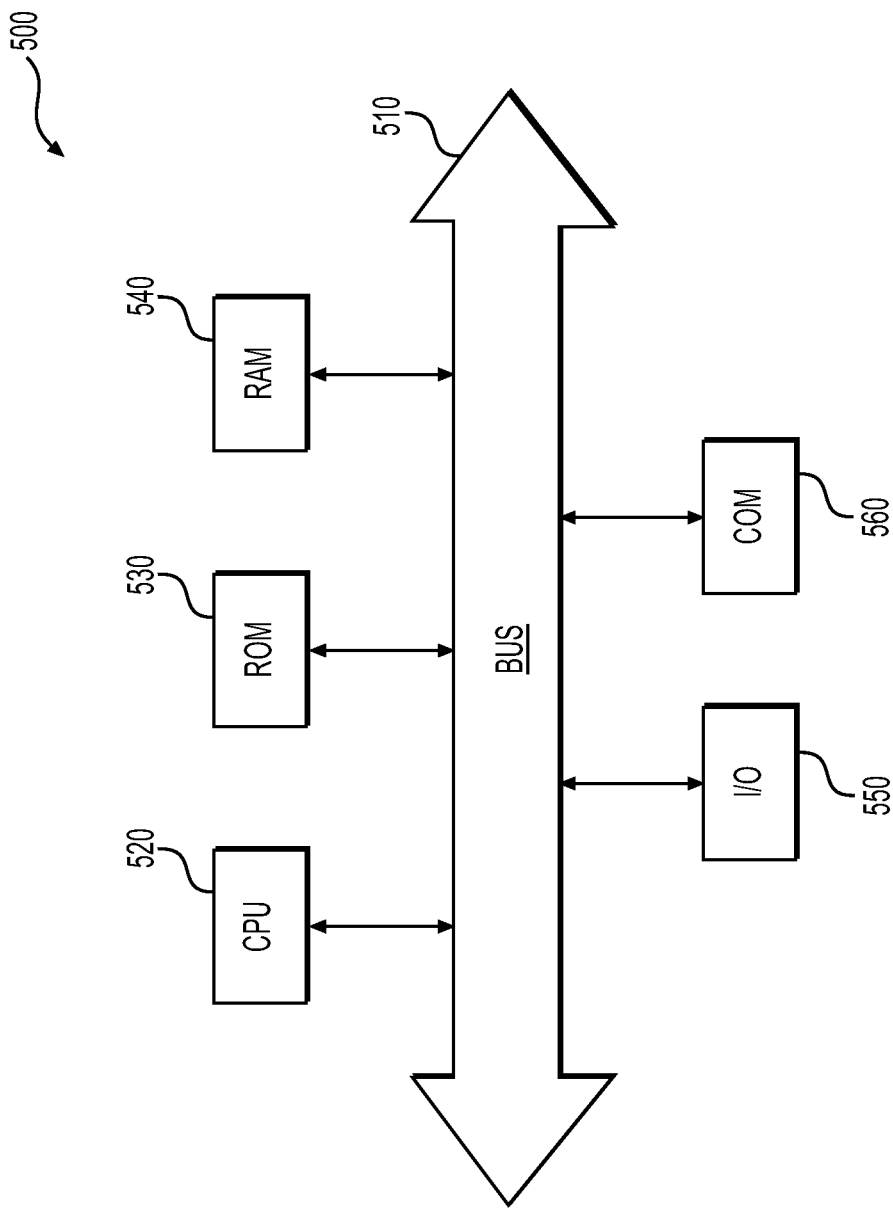
FIG. 5 illustrates an example system that may execute techniques presented herein.

As shown in FIG. 5, device 500 may include a central processing unit (CPU) 520. CPU 520 may be any type of processor device including, for example, any type of special purpose or a general-purpose microprocessor device. As will be appreciated by persons skilled in the relevant art, CPU 520 also may be a single processor in a multi-core/multi-processor system, such system operating alone, or in a cluster of computing devices operating in a cluster or server farm. CPU 520 may be connected to a data communication infrastructure 510, for example a bus, message queue, network, or multi-core message-passing scheme.

Device 500 may also include a main memory 540, for example, random access memory (RAM), and also may include a secondary memory 530. Secondary memory 530, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 530 may include similar means for allowing computer programs or other instructions to be loaded into device 500. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 500.

Device 500 may also include a communications interface ("COM") 560. Communications interface 560 allows software and data to be transferred between device 500 and external devices. Communications interface 560 may include a modem, a network interface (such as an Ethernet card), a communications port, a PCMCIA slot and card, or the like. Software and data transferred via communications interface 560 may be in the form of signals, which may be electronic, electromagnetic, optical or other signals capable of being received by communications interface 560. These signals may be provided to communications interface 560 via a communications path of device 500, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith, Device 500 may also include input and output ports 550 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention may be apparent to those skilled in the art from consideration of the specification and practice of the invention disclosed herein. It is intended that the specification and examples be considered as exemplary only.

What is claimed is:

1. A computer-implemented method for providing automated routing of medical data, the method comprising:
   determining at least one rule corresponding to at least one condition and at least one receiver;
   receiving medical data and associated medical metadata;
   determining a quality score for the medical data and the associated medical metadata, the medical data comprising at least one image, the quality score identifying quality control issues in the medical data and the associated medical metadata that affect the usability of the medical data and the associated medical metadata for making a diagnosis;
   outputting a prediction of the diagnosis from artificial intelligence processing;
   determining, after outputting the prediction of the diagnosis, whether the medical data, the associated medical metadata, and/or associated artificial intelligence processing satisfies the at least one condition of the at least one rule based at least in part on the quality score, the at least one condition comprising output from the artificial intelligence processing related to the artificial intelligence processing being unable to make the diagnosis on the medical data and the associated medical metadata with a level of confidence, the level of confidence being based at least in part on the quality score; and
   upon determining that the at least one condition of the at least one rule is satisfied, providing, from an originating institution, the medical data to the at least one receiver.

2. The computer-implemented method of claim 1, further comprising:
   receiving, in response to the providing, a report from the at least one receiver of the at least one rule.

3. The computer-implemented method of claim 1, wherein the associated artificial intelligence processing comprises an artificial intelligence based assessment of the medical data.

4. The computer-implemented method of claim 3, further comprising:
upon the artificial intelligence based assessment of the medical data determining that it cannot accurately diagnose the medical data, providing the medical data to at least one expert.

5. The computer-implemented method of claim 3, wherein the associated artificial intelligence processing provides the medical data to at least one expert in response to detecting a lack of expertise in the originating institution.

6. The computer-implemented method of claim 1, wherein the at least one image comprises at least one whole slide image and/or at least one static image, and wherein the medical data further comprises at least one patient medical record, at least one physician note, at least one radiological scan, at least one dental note, and/or at least one lab result.

7. The computer-implemented method of claim 1, wherein the at least one condition further comprises at least one disease type, at least one tissue type, at least one location of a sample, and/or at least one physician assigned to review the medical data at the originating institution.

8. The computer-implemented method of claim 1, wherein the associated medical metadata comprises at least one medical disease type, at least one medical tissue type, at least one medical location of a sample, and/or at least one medical physician assigned to review the medical data.

9. A computer system for providing automated routing of medical data, the computer system comprising:
at least one memory storing instructions; and
at least one processor configured to execute the instructions to perform operations comprising:
access the at least one memory and execute processor-readable instructions, which when executed by the at least one processor configures the at least one processor to perform a plurality of functions, including functions for:
determining at least one rule corresponding to at least one condition and at least one receiver;
receiving medical data and associated medical metadata;
determining a quality score for the medical data and the associated medical metadata, the medical data comprising at least one image, the quality score identifying quality control issues in the medical data and the associated medical metadata that affect usability of the medical data and the associated medical metadata for making a diagnosis;
output a prediction of the diagnosis from artificial intelligence processing;
determining, after outputting the prediction of the diagnosis, whether the medical data, the associated medical metadata, and/or associated artificial intelligence processing satisfies the at least one condition of the at least one rule based at least in part on the quality score, the at least one condition comprising output from the artificial intelligence processing related to the artificial intelligence processing being unable to make the diagnosis on the medical data and the associated medical metadata with a level of confidence, the level of confidence being based at least in part on the quality score; and
upon determining that the at least one condition of the at least one rule is satisfied, providing, from an originating institution, the medical data to the at least one receiver.

10. The computer system of claim 9, the operations further comprising:
receiving, in response to the providing, a report from the at least one receiver of the at least one rule.

11. The computer system of claim 9, wherein the associated artificial intelligence processing comprises an artificial intelligence based assessment of the medical data.

12. The computer system of claim 11, further comprising:
upon the artificial intelligence based assessment of the medical data determining that it cannot accurately diagnose the medical data, providing the medical data to at least one expert.

13. The computer system of claim 11, wherein the associated artificial intelligence processing provides the medical data to at least one expert in response to detecting a lack of expertise in the originating institution.

14. The computer system of claim 9, wherein the at least one condition further comprises at least one disease type, at least one tissue type, at least one location of a sample, and/or at least one physician assigned to review the medical data at the originating institution.

15. The computer system of claim 9, wherein the associated medical metadata comprises at least one medical disease type, at least one medical tissue type, at least one medical location of a sample, and/or at least one medical physician assigned to review the medical data.

16. A non-transitory computer-readable medium storing instructions that, when executed by a processor, cause the processor to perform operations for providing automated routing of medical data, the operations comprising:
determining at least one rule corresponding to at least one condition and at least one receiver;
receiving medical data and associated medical metadata;
determining a quality score for the medical data and the associated medical metadata, the medical data comprising at least one image, the quality score identifying quality control issues in the medical data and the associated medical metadata that affect usability of the medical data and the associated medical metadata for making a diagnosis;
outputting a prediction of the diagnosis from artificial intelligence processing;
determining, after outputting the prediction of the diagnosis, whether the medical data, the associated medical metadata, and/or associated artificial intelligence processing satisfies the at least one condition of the at least one rule based at least in part on the quality score, the at least one condition comprising output from the artificial intelligence processing related to the artificial intelligence processing being unable to make the diagnosis on the medical data and the associated medical metadata with a level of confidence, the level of confidence being based at least in part on the quality score; and
upon determining that the at least one condition of the at least one rule is satisfied, providing, from an originating institution, the medical data to the at least one receiver.

17. The non-transitory computer-readable medium of claim 16, further comprising:
receiving, in response to the providing, a report from the at least one receiver of the at least one rule.

18. The non-transitory computer-readable medium of claim 16, wherein the associated artificial intelligence processing comprises an artificial intelligence based assessment of the medical data.

19. The non-transitory computer-readable medium of claim 18, further comprising:
   upon the artificial intelligence based assessment of the medical data determining that it cannot accurately diagnose the medical data, providing the medical data to at least one expert.

20. The non-transitory computer-readable medium of claim 18, wherein the associated artificial intelligence processing provides the medical data to at least one expert in response to detecting a lack of expertise in the originating institution.

* * * * *